(12) United States Patent
Desarbre et al.

(10) Patent No.: US 8,809,315 B2
(45) Date of Patent: Aug. 19, 2014

(54) COMBINATION MEDICAMENTS FOR TREATING BACTERIAL INFECTIONS

(71) Applicant: Basilea Pharmaceutica AG, Basel (CH)

(72) Inventors: Eric Desarbre, Mulhouse (FR); Malcolm G. P. Page, Basel (CH)

(73) Assignee: Basilea Pharmaceutica AG, Basel (CH)

( * ) Notice: Subject to any disclaimer, the term of this patent is extended or adjusted under 35 U.S.C. 154(b) by 0 days.

(21) Appl. No.: 13/915,833

(22) Filed: Jun. 12, 2013

(65) Prior Publication Data

US 2013/0274238 A1 Oct. 17, 2013

Related U.S. Application Data

(62) Division of application No. 12/532,243, filed as application No. PCT/EP2008/053336 on Mar. 19, 2008, now Pat. No. 8,486,929.

(30) Foreign Application Priority Data

Mar. 23, 2007 (EP) .................................. 07006053

(51) Int. Cl.
| | |
|---|---|
| A01N 43/00 | (2006.01) |
| A01N 43/40 | (2006.01) |
| A01N 43/64 | (2006.01) |
| A01N 43/78 | (2006.01) |
| A61K 31/397 | (2006.01) |
| A61K 31/00 | (2006.01) |
| A61K 31/435 | (2006.01) |
| A61K 31/41 | (2006.01) |
| A61K 31/425 | (2006.01) |

(52) U.S. Cl.
USPC ............ 514/210.01; 514/210.02; 514/210.03; 514/277; 514/365

(58) Field of Classification Search
CPC . A61K 31/381; A61K 31/397; A61K 31/426; A61K 31/435
USPC .......... 514/210.01, 210.02, 210.03, 277, 359, 514/365
See application file for complete search history.

(56) References Cited

U.S. PATENT DOCUMENTS 8,486,929 B2 * 7/2013 Desarbre et al. .......... 514/210.01

FOREIGN PATENT DOCUMENTS

| WO | WO 02/22613 | * | 3/2002 |
| WO | WO 2007/065288 | * | 6/2007 |

* cited by examiner

*Primary Examiner* — Yong Chong

(57) ABSTRACT

Use of a monobactam antibiotic of formula (I)

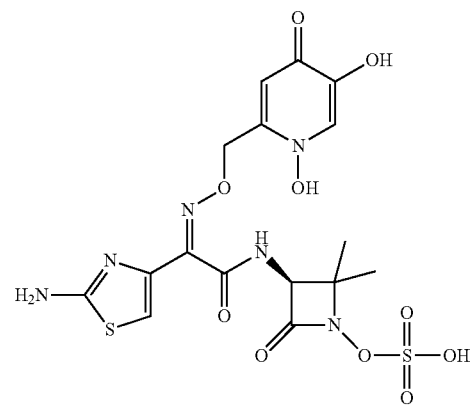

wherein the oxyimino group i.e. >C=N—O— has Z-orientation, or a pharmaceutically acceptable salt thereof for the manufacture of a medicament for the treatment of a bacterial infection in combination with a carbapenem antibiotic or a pharmaceutically acceptable salt thereof.

20 Claims, 1 Drawing Sheet

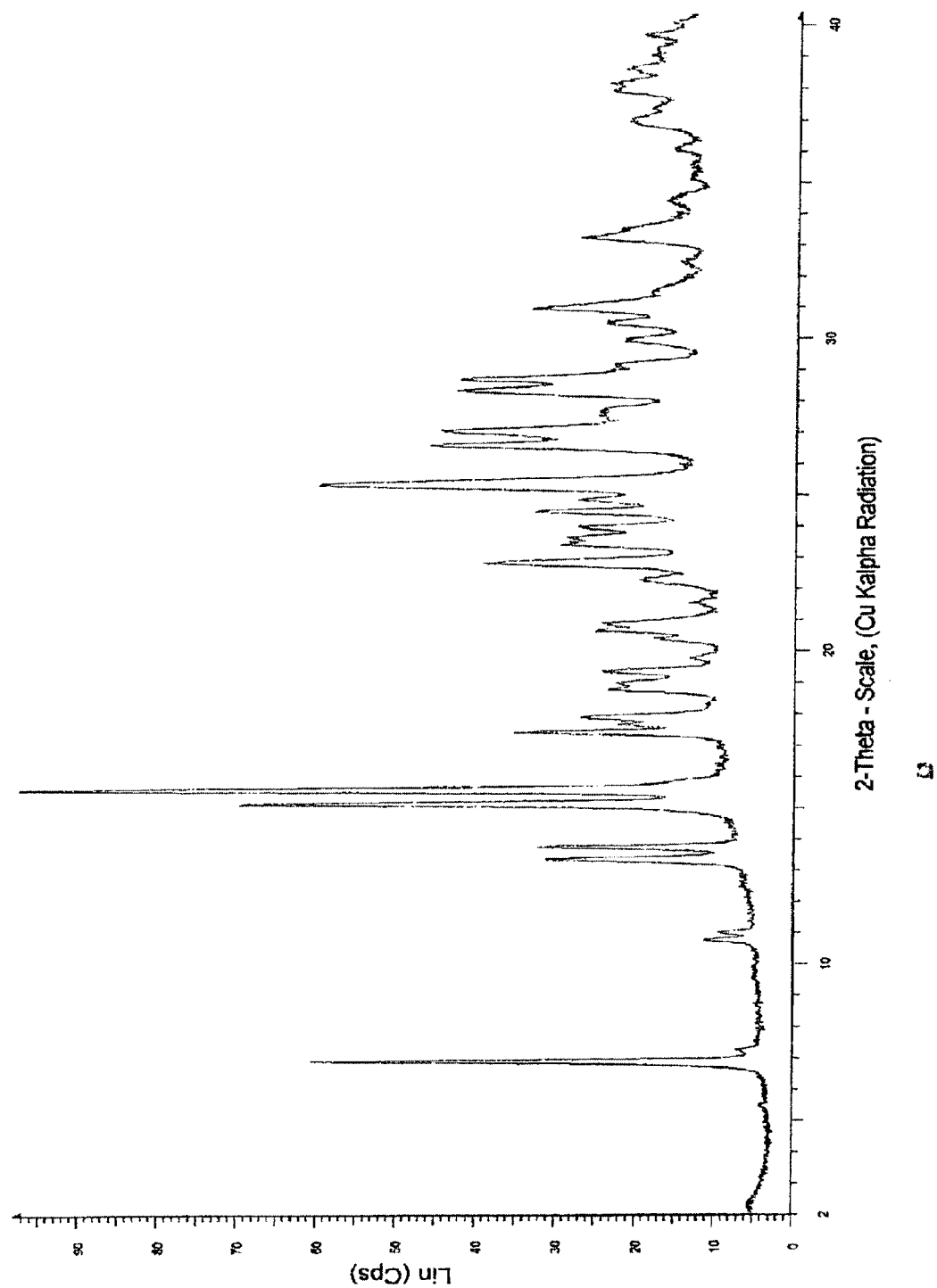

COMBINATION MEDICAMENTS FOR TREATING BACTERIAL INFECTIONS

CROSS-REFERENCE TO RELATED APPLICATIONS

This Application is a divisional application of application Ser. No. 12/532,243, filed on Sep. 21, 2009, which is a National Stage Application of PCT/EP2008/053336, filed Mar. 19, 2008, which claims priority from European Patent Application 07006053.8, filed on Mar. 23, 2007. Each of prior mentioned applications is hereby incorporated by reference herein in its entirety.

The present invention relates to the use of monobactam antibiotic of formula (I) as described herein below and novel pharmaceutical products comprising a combination comprising said compound and a carbapenem antibiotic.

β-Lactam antibiotics have been widely used for the treatment of bacterial infections both in hospitals and in the general public. There are several classes of β-lactam antibiotics that have found clinical application, these include the penicillins, cephalosporins, cephamycins, carbacephems, oxacephems, carbapenems and monobactams.

The efficiency of all of these classes to cure bacterial infections has been impaired by the appearance of bacteria that are resistant towards the antibiotics. The prevalent cause of this resistance in Gram-negative bacteria is the expression by the bacteria of enzymes known as β-lactamases that are able to hydrolyse the β-lactam antibiotics rendering them inactive. Bacteria are able to produce a variety of β-lactamases, including penicillinases, cephalosporinases, cephamycinases, carbapenemases, monobactamases, broad-spectrum β-lactamases and extended-spectrum β-lactamases.

Monobactam antibiotics (e.g. aztreonam) have been regarded as stable towards many β-lactamases. Nevertheless there are many strains of Gram-negative bacteria that now exhibit β-lactamase-mediated resistance towards aztreonam.

Combinations between Aztreonam, i.e. (Z)-2-[[[(2-amino-4-thiazolyl)[[(2S,3S)-2-methyl-4-oxo-1-sulfo-3-azetidinyl]-carbamoyl]methylene]amino]oxy]-2-methylpropionic acid, and carbapenems (Imipenem or Meropenem) have been investigated as a possible way to overcome bacterial resistance. Although some synergy between aztreonam and a carbapenem was observed against bacteria belonging to the Enterobacteriaceae [Sader H S, Huynh H K, Jones R N; Contemporary in vitro synergy rates for aztreonam combined with newer fluoroquinolones and β-lactams tested against Gram-negative bacilli; Diagn. Microbiol. Infect. Dis. 47 (2003) 547-550], the activity of the combinations against *Pseudomonas aeruginosa* was devoid of synergy or even showed antagonism [Sader H S, Huynh H K, Jones R N; Contemporary in vitro synergy rates for aztreonam combined with newer fluoroquinolones and β-lactams tested against Gram-negative bacilli; Diagn. Microbiol. Infect. Dis. 47 (2003) 547-550; Yamaki K, Tanaka T, Takagi K, Ohta M; Effects of aztreonam in combination with antipseudomonal antibiotics against *Pseudomonas aeruginosa* isolated from patients with chronic or recurrent lower respiratory tract infection. J. Infect. Chemother. 4 (1998) 50-55].

WO 98/47895 is directed to 2-oxo-1-azetidine sulfonic acid derivatives of the general formula

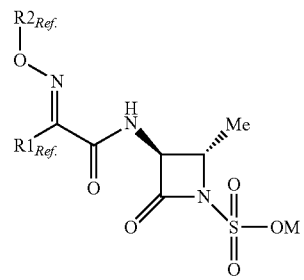

wherein the oxyimino fragment

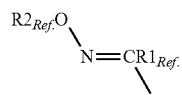

has 'anti' orientation as shown in the above formula. 'anti' is an older term used to designate the trans-isomer of an oxime compound (the prefix 'syn' was accordingly used to designate the cis of an oxime); cf. IUPAC Gold Book; IUPAC Compendium of Chemical Terminology, Electronic version, http://goldbook.iupac.org/E0204.html and PAC, 1996, 68, 2193 *Basic terminology of stereochemistry (IUPAC Recommendations* 1996) on page 2207. The disclosed 2-oxo-1-azetidine sulfonic acid derivatives are to be used in combination with carbapenem antibiotics including Imipenem, Meropenem or Biapenem for the treatment of bacterial infections. $R1_{Ref}$ is preferably a 2-thienyl group and is used in all exemplified inventive compounds of said reference. $R2_{Ref}$ can among other groups e.g. be a group of formula:

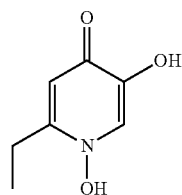

The 'anti' (trans) orientation of the oxyimino fragment is described to provide excellent synergy with ceftazidime. Example 1 of the reference e.g. refers to (3S)-trans-3-[(E)-2-(2-thienyl)-2-{(1,5-dihydroxy-4-pyridon-2-ylmethoxy)imino}-acetamido]-4-methyl-2-oxazetidine-1-sulfonic acid and is shown to have, together with ceftazidime, antibacterial activity against numerous strains of pathogenic bacteria.

There is however an increasing formation of resistance towards conventional monobactam antibiotics, like e.g. Aztreonam. Particularly in view of this growing resistance, there is an ongoing need for novel alternatives to known monobactam antibiotics as well as for finding novel antibiotic combinations.

This invention is based on the recent finding of novel monobactam antibiotics and, more particularly, on the novel finding that a specific embodiment of these monobactams, the monobactam antibiotic of formula (I) as described herein below, when used in combination with other antibiotics, in particular carbapenem antibiotics, shows improved efficacy against a broad range of bacteria, including Gram-positive and especially Gram-negative bacteria, including *Enterobac-* teriaceae and *Pseudomonas aeruginosa*. In particular, the efficacy of the novel combinations of the monobactam antibiotic of formula (I) with carbapenem antibiotics is for many strains of important pathogenic bacteria significantly improved with regard to combinations of Aztreonam with the respective carbapenem antibiotics, e.g. the combinations of Aztreonam with Meropenem or Imipenem.

Furthermore, the combinations of the present invention frequently exhibit a significantly improved efficacy against bacteria when compared to the best efficacy of the combination partners alone, and frequently exhibits a synergistic effect i.e. an effect which is more potent than what one would expect from a purely additive effect.

Thus the present invention relates to the use of the monobactam antibiotic of formula (I)

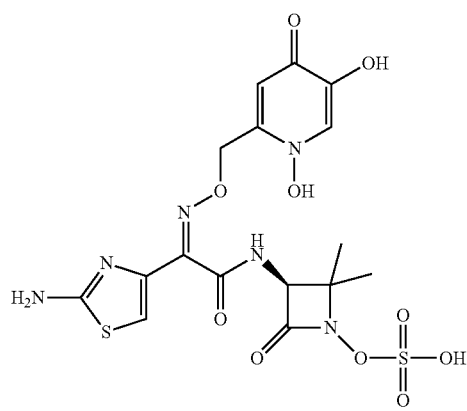

(I)

wherein the oxyimino group, i.e. >C=N—O— is in Z-orientation, (corresponding to the =cis-orientation or syn-orientation in the sense indicated above with regard to WO 98/47895), or a pharmaceutically acceptable salt thereof for the manufacture of a medicament for the treatment of a bacterial infection in combination with one or more than one carbapenem antibiotic, or pharmaceutically acceptable salts thereof.

In another aspect the invention relates to pharmaceutical products comprising a monobactam antibiotic of formula (I) as described above or a pharmaceutically acceptable salt thereof and one or more than one carbapenem antibiotic, or pharmaceutically acceptable salt thereof.

These pharmaceutical products represent improved medicaments for the treatment of infections caused by pathogenic bacteria, including Gram-positive and particularly Gram-negative bacteria.

Particularly preferred according to the invention is the use of the monobactam antibiotic of formula (I) or a salt thereof for the manufacture of a medicament for the treatment of a bacterial infection in combination with a single carbapenem antibiotic, or a pharmaceutically acceptable salt thereof.

The monobactam antibiotic of formula (I) can e.g. be prepared according to the following general Scheme 1:

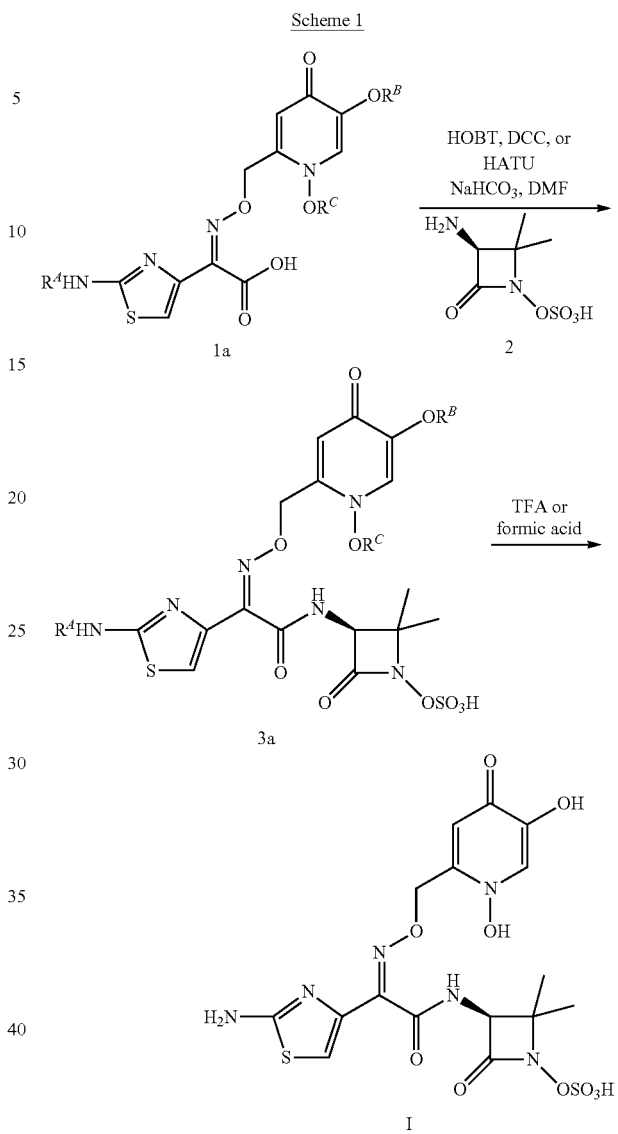

Scheme 1 wherein "HOBT" stands for "hydroxybenzotriazole", "DCC" for "dicyclohexylcarbodiimide" and "TFA" for "trifluoroacetic acid". The reaction of compound of general formula 1a and compound 2 according to said scheme is described in Org. Process Res. & Dev. 2002, 863. Alternatively, the coupling reaction of compound of general formula 1a with compound 2 can e.g. be performed with the corresponding acyl chloride (Chem. Pharm. Bull. 1983, 2200) or with an activated ester of compound 1, such as the N-hydroxysuccinimidyl ester (see Org. Process Res. & Dev. 2002, 863), or the benzothiazolyl thioester (see J. Antibiotics 2000, 1071). Alternatively, other coupling reagents, such as hydroxyazabenzotriazole (HOAT), 2-(1H-7-azabenzotriazol-1-yl)-1,1,3,3-tetramethyl uronium hexafluorophosphate methanaminium (HATU), O-BenzotriazoleN,N,N',N'-tetramethyl-uronium-hexafluoro-phosphate (HBTU), used for amino acid coupling reactions, can replace hydroxybenzotriazole (HOBT) or benzotriazolyloxytris (dimethylamino) phosphonium hexafluorophosphate (PyBOP) (For more detail on suitable coupling reagents, see N. Sewald, H.-D. Jakubke, Peptides: Chemistry and Biology, Wiley-VCH, 2002).

The preparation of compound of general formula 1a can be carried out in a customary way by reacting the appropriate keto acid 1-A3 with the appropriately etherified hydroxylamine 1-A4 as shown in Scheme 2 below:

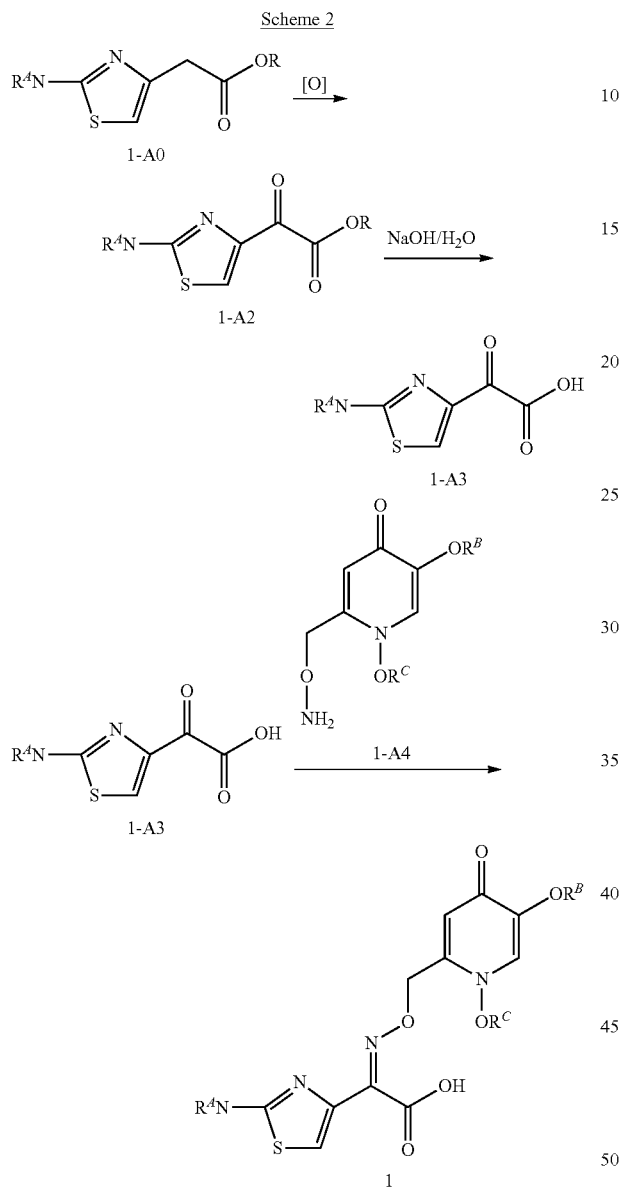

In the above scheme 2, the preparation of compound 1-A4 from kojic acid and its reaction with compound 1-A3 are described in detail e.g. in EP-A-0 251 299. Compound 1-A3 can be obtained starting from compound 1-A0 as shown in the upper part of above scheme 2. The compounds 1-A0 can be prepared according to known methods and are partially commercially available, e.g. ethyl 2-(2-amino-1,3-thiazol-4-yl) acetate (R in formula 1-A0=ethyl) from CHEMOS GmbH, 93128 Regenstauf, Germany). The oxidation of 1-A0 to 1-A2 with e.g. selenium dioxide may be performed in analogy to the oxidation described in the second step of example 1 of GB-A-1 575 804.

Compound 2 of Scheme 1 can e.g. be manufactured according to the route in Scheme 3:

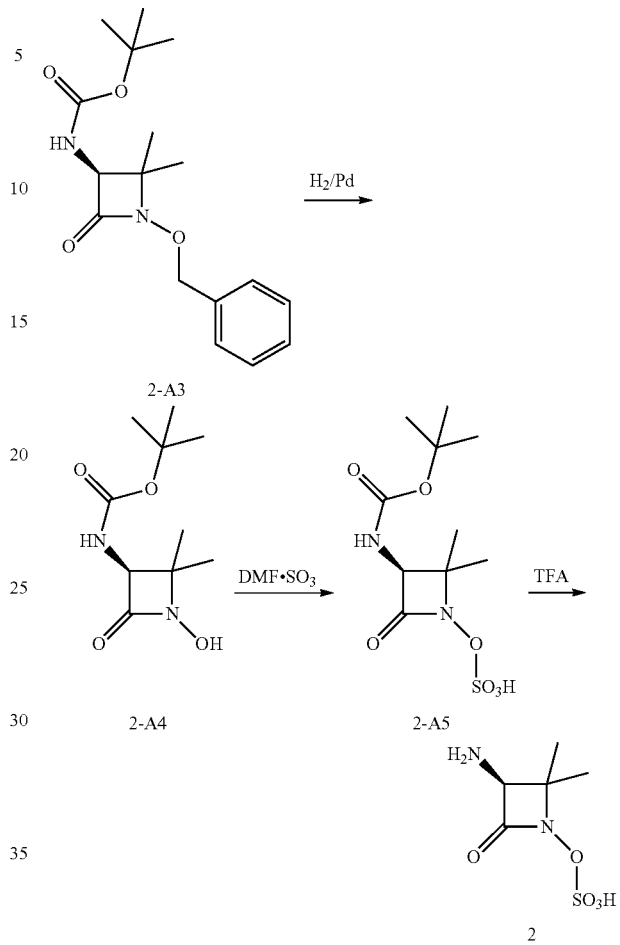

wherein "DMF SO$_3$" stands for the dimethylformamide-sulphur trioxide complex and "TFA" for trifluoroacetic acid. In the above scheme 3, starting material 2-A3 can be prepared as described on page 2790 of Tetrahedron Lett. 1986, p. 2789-2792 (a direct synthesis for the optically active (S)—N-Boc-3-hydroxyvaline, required in turn there as the starting material, can be found in the last example of J. Org. Chem. 2003, 68, p. 177-179). The conversions from 2-A3 to 2-A4, to 2-A5 and to 2 are described in more detail e.g. in the examples of J. Antibiotics, 1985, p. 1536-1549 (see Scheme 1 of said reference).

In scheme 1 above

R$^A$ represents an amine protecting group such as formyl, trifluoroacetyl, O-nitrophenoxyacetyl, chloroacetyl, trichloroacetyl, γ-chlorobutyryl, benzyloxycarbonyl, pchlorobenzyloxycarbonyl, p-nitrobenzyloxycarbonyl, pbromobenzyloxycarbonyl, p-methoxybenzyloxycarbonyl, diphenylmethoxycarbonyl, ter-butyloxycarbonyl, isopropyloxycarbonyl, diphenylmethyl, triphenylmethyl, benzyl, p-methoxybenzyl, 3,4-dimethoxybenzyl; and R$^B$ and R$^C$ represent independently of one another an alcohol protecting group such as benzyloxycarbonyl, pchlorobenzyloxycarbonyl, p-nitrobenzyloxycarbonyl, pbromobenzyloxycarbonyl, p-methoxybenzyloxycarbonyl, diphenylmethoxycarbonyl, ter-butyloxycarbonyl, isopropyloxycarbonyl, diphenylmethyl, triphenylmethyl, benzyl, p-methoxybenzyl, 3,4-dimethoxybenzyl, trialkylsilane such as trimethylsilane, triethylsilane or ter-butyldimethylsilane.

Said amine and alcohol protecting groups can be easily removed, e.g. by acid hydrolysis or other well known techniques. [for more detail see e.g. T. W. Greene et al. Protective Groups in Organic Chemistry, Wiley intersience, 1999]. The protecting groups in compounds of general formula 1a can easily be introduced by well known synthetic methods. [for more detail see e.g. T. W. Greene et al. Protective Groups in Organic Chemistry, Wiley intersience, 1999].

The deprotection of functional groups may be carried out either by hydrogenation or hydrolysis with appropriate acids, such as hydrochloric acid, formic acid, acetic acid, trifluoroacetic acid, phosphoric acid, NaH $PO_4$, Na $HPO_4$, ptoluenesulfonic acid or methanesulfonic acid, in solvents such as methanol, ethanol, propanol, ethyl acetate, acetonitrile, methylene chloride or ethylene chloride. The hydrogenation is usually carried out in the presence of a metal catalyst, such as Pd, Pt or Rh under normal to high pressure. The deprotection of the different functional groups can be carried out either simultaneously or sequentially.

The solvents of choice for the reaction are selected based upon the reactants used and from solvents such as benzene, toluene, acetonitrile, tetrahydrofurane, ethanol, methanol, chloroform, ethyl acetate, methylene chloride, dimethyl formamide, dimethyl sulfoxide, hexamethyl phosphoric triamide or the like. Solvents mixtures may also be used.

Reaction temperatures would generally range from between −70° C. to 150° C. The preferred molar ratio of the reactants is 1:1 to 1:5. The reaction time range from 0.5 to 72 hours, depending on the reactants.

Examples of pharmaceutically acceptable salts of the compound of formula (I) include e.g. salts of inorganic base like ammonium salts, alkali metal salts, in particular sodium or potassium salts, alkaline earth metal salts, in particular magnesium or calcium salts; salts of organic bases, in particular salts derived from cyclohexylamine, benzylamine, octylamine, ethanolamine, diethylolamine, diethylamine, triethylamine, ethylendiamine, procaine, morpholine, pyrroline, piperidine, N-ethylpiperidine, N-methylmorpholine, piperazine as the organic base; or salts with basic amino acids, e.g. lysine, arginine, ornithine, histidine and the like.

Such salts can be manufactured in a way known per se, e.g. by reacting the compound of formula (I) with an appropriate base, preferably at room temperature or below, e.g. from about 2° C. to about 25° C. and isolating the salt formed, e.g. by lyophilization.

The compounds of formula (I) are optionally used in substantially crystalline form. A substantially crystalline compound of formula (I) has not yet been described before. It can be obtained by crystallisation methods, e.g. as described in the Examples of the present application. For the purposes of this application the term "substantially crystalline" means that an X-Ray Powder Diffraction (XRPD) diagram of a corresponding substance shows one or more distinct peaks which have a maximum height corresponding to at least the fivefold of their width at half-maximum. Generally, the degree of crystallinity of a substance increases with an increasing average value for the ratio of the height of a certain peak to its width at half-maximum. Furthermore, the XRPD diagram shall show a substantially constant base line (baseline=a line connecting the minima of the XRPD diagram curve) over the entire scanned 2-theta range, indicating the substantial absence of amorphous material. in the recorded sample. "Substantially constant base line" means for the purposes of this application that the baseline does preferably not rise for more than the height of the lowest peak of said diagram.

A further subject of the present invention is therefore the compound of formula (I) being in substantially crystalline form.

Said substantially crystalline compound of formula (I) shows peaks in the X-Ray Powder Diffractogram (XRPD) having a relative Intensity of more than 50%, recorded with Cu K-alpha Radiation and given in [°2-Theta], at about 6.8±0.1, 15.1±0.1, 15.6±0.1 and 25.4±0.1, and exhibits a X-Ray Powder Diffraction pattern, recorded with Cu K-alpha radiation, essentially as follows:

| 2Θ [° ± 0.1°] | Rel Int |
|---|---|
| 6.86 | m |
| 13.32 | w |
| 13.72 | w |
| 15.11 | st |
| 15.57 | vst |
| 22.84 | w |
| 25.37 | m |
| 26.32 | w |
| 27.08 | w |
| 28.38 | w |
| 28.74 | w | wherein vst stands for a relative intensity of 100% to 90%; st stands for a relative intensity of less than 90% to 65%; m stands for a relative intensity of less than 65% to 50%; and w stands for a relative intensity of less than 50% to 30%, more specifically the following X-Ray Powder Diffraction pattern recorded with Cu K-alpha radiation and indicating the diffraction peaks with a relative Intensity of 20% and more:

| 2Θ [° ± 0.1°] | Rel Int ** |
|---|---|
| 6.86 | 64 ± 13 |
| 13.32 | 27 ± 6 |
| 13.72 | 28 ± 6 |
| 15.11 | 69 ± 14 |
| 15.57 | 100 ± 20 |
| 17.41 | 29 ± 6 |
| 17.88 | 20 ± 4 |
| 22.84 | 31 ± 6 |
| 24.49 | 22 ± 4 |
| 25.37 | 52 ± 10 |
| 26.32 | 36 ± 7 |
| 27.08 | 34 ± 7 |
| 28.38 | 33 ± 7 |
| 28.74 | 32 ± 6 |
| 31.00 | 23 ± 5 |

** with typical variation of the indicated values for the relative intensity

It is known that the values for the relative Intensity of the peaks are more strongly dependent from certain properties of the measured sample than the line position, e.g. from the size of the crystals and/or their orientation in the sample. Variations of about ±20% of the shown peak intensities are therefore likely to occur.

FIG. 1 shows the XRPD diagram of typical crystalline material of the compound of formula (I) recorded with Cu K-alpha radiation.

The compound of formula (I) and its pharmaceutically compatible salts are used according to the invention in combination with other antibiotics like in particular carbapenem antibiotics or pharmaceutically acceptable salts thereof as antibiotically effective medicaments in the control or prevention of infectious diseases in mammals, human and non-human, in particular bacterial infections, more particularly infections in which Gram-positive bacteria and mostly preferred in which Gram-negative bacteria are involved, such as e.g. nosocomial pneumonia, community-acquired pneumonia, urinary tract infection, complicated intra-abdominal infection, complicated skin/skin structure infection, infectious exacerbations of cystic fibrosis, sepsis, melioidosis.

In this sense, the compound of formula (I) and its pharmaceutically acceptable salts are used according to the invention in combination with a carbapenem antibiotic or pharmaceutically acceptable salt thereof for such treatment. Although not preferred, there may be certain situations, wherein the use of compound (I) or a salt thereof with two or even more different carbapenem antibiotics may be of advantage and indicated.

For the purposes of this application, the term "carbapenem antibiotic" refers to antibiotically effective compounds comprising the structural element:

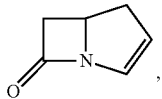

Numerous carbapenem antibiotics are known in the art, and can, in general, be used for the purposes of the present invention. Suitable examples are described e.g. in A. BRYSKIER "Carbapenems", ANTIMICROBIAL AGENTS: ANTIBACTERIALS AND ANTIFUNGALS, page 270-321, Publisher: American Society for Microbiology, Washington D.C., 2005, and references cited therein. The term "carbapenem antibiotic" includes inner salts like e.g. ME 1036 or Biapenem.

In addition to the mentioned inner salts other pharmaceutically acceptable salts of carbapenem antibiotics may also be used for the purposes of the present invention, e.g. acid addition salts derived from pharmaceutically acceptable organic and/or inorganic acids.

Preferably, the carbapenem antibiotics used according to the present invention, are compounds of formula (II), or pharmaceutically acceptable salt thereof:

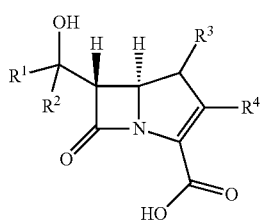

(II)

wherein
$R^1$ represents hydrogen or $C_1$-$C_6$alkyl;
$R^2$ represents hydrogen or $C_1$-$C_6$alkyl;
$R^3$ represents hydrogen, $C_1$-$C_6$alkyl, $C_1$-$C_6$alkoxy; —$(C_{1n}H_{2n})$—$R^5$ or —O—$(C_{1n}H_{2n})$—$R^5$;
wherein
$R^5$ represents halogen, cyano, $C_1$-$C_6$alkoxy, amino, ($C_1$-$C_6$alkyl)amino, di($C_1$-$C_6$alkyl)amino, or a group of formula —CO—$R^6$, —NH—CO—$R^6$—CO—$NH_2$, —NH—CO—$NH_2$, —NH—$SO_2$—$NH_2$ or —NH—(C=NH)—$NH_2$, in which groups one or more of the hydrogen atoms may also be replaced with $R^6$ or the —$NH_2$ residue of the group can be replaced with a 5-6 membered heterocyclic ring bound to the group via a nitrogen atom present in the ring which heterocyclic ring may be unsubstituted or substituted with one or more of a substituent $S^2$, wherein each $S^2$ has independently of other substituents $S^2$ one of the meanings defined below; and $R^6$ represents $C_1$-$C_6$alkyl, phenyl or a 5-6 membered heterocyclic ring and may be unsubstituted or substituted with one or more of a substituent $S^1$, wherein each $S^1$ has independently of other substituents $S^1$ one of the meanings defined below; and n is an integer from 1 to 6;
$R^4$ represents a group of formula —$(S)_m$—$R^7$, wherein m is 0 or 1 and $R^7$ represents hydrogen; $C_1$-$C_6$alkyl, unsubstituted or substituted with one or more of a substituent $S^1$; phenyl, unsubstituted or substituted with one or more of a substituent $S^1$; or a 3-6 membered heterocyclyl group containing one or more than one heteroatom selected from nitrogen, sulfur and oxygen, which heterocyclyl group may furthermore optionally be fused to a phenyl ring or a 5-6 membered heterocyclic ring and which whole group is unsubstituted or substituted with one or more of a substituent $S^1$; wherein each $S^1$ is independently of other substituents $S^1$ selected $C_1$-$C_6$alkyl, unsubstituted or substituted with one or more of a substituent $S^2$; phenyl, unsubstituted or substituted with one or more of a substituent $S^2$; or a 3-6 membered heterocyclyl group containing one or more than one heteroatom selected from nitrogen, sulfur and oxygen, which heterocyclyl group may furthermore optionally be fused to a phenyl ring or a 5-6 membered heterocyclic ring and which whole group is unsubstituted or substituted with one or more of a substituent $S^2$; $C_1$-$C_6$alkoxy, hydroxyl, carboxy, amino, $C_1$-$C_6$alkyl amino, di($C_1$-$C_6$)alkyl amino, cyano, halogen, or a group of formula CO—$R^8$, —NH—CO—$NH_2$, —CO—$NH_2$, —NH—CH=NH, —(C=NH)—$C_1$-$C_6$alkyl, —NH—CO—$NH_2$, —NH—$SO_2$—$NH_2$ or —NH—(C=NH)—$NH_2$, in which groups one or more of the hydrogen atoms may also be replaced with $R^8$ or the —$NH_2$ residue of the group can be replaced with a 5-6 memtiered heterocyclic ring bound to the group via a nitrogen atom present in the ring which heterocyclic ring may be unsubstituted or substituted with one or more of a substituent $S^2$, wherein each $S^2$ has independently of other substituents $S^2$ one of the meanings defined below; and $R^8$ represents $C_1$-$C_6$alkyl, unsubstituted or substituted with one or more of a substituent $S^2$; phenyl, unsubstituted or substituted with one or more of a substituent $S^2$; or a 3-6 membered heterocyclyl group containing one or more than one heteroatom selected from nitrogen, sulfur and oxygen, which heterocyclyl group may furthermore optionally be fused to a phenyl ring or a 5-6 membered heterocyclic ring and which whole group is unsubstituted or substituted with one or more of a substituent $S^2$, wherein each $S^2$ is independently from other substituents $S^2$ selected from $C_1$-$C_6$alkyl, unsubstituted or substituted with one or more of a substituent $S^3$; phenyl, unsubstituted or substituted with one or more of a substituent $S^3$; or a 3-6 membered heterocyclyl group containing one or more than one heteroatom selected from nitrogen, sulfur and oxygen, which heterocyclyl group may furthermore optionally be fused to a phenyl ring or a 5-6 membered heterocyclic ring and which whole group is unsubstituted or substituted with one or more of a substituent $S^3$; $C_1$-$C_6$alkoxy, hydroxyl, carboxy, amino, $C_1$-$C_6$alkyl amino, di($C_1$-$C_6$)alkyl amino, cyano, halogen, or a group of formula —CO—$R^9$, —NH—CO—$R^9$; —CO—

$NH_2$, —NH—CH=NH, —NH—CO—$NH_2$, —NH—$SO_2$—$NH_2$ or —NH—(C=NH)—$NH_2$, in which groups one or more of the hydrogen atoms may also be replaced with $R^9$ or the —$NH_2$ residue of the group can be replaced with a 5-6 membered heterocyclic ring bound to the group via a nitrogen atom present in the ring which heterocyclic ring may be unsubstituted or substituted with one or more of a substituent $S^3$, wherein each $S^3$ has independently of other substituents $S^3$ one of the meanings defined below; and $R^9$ represents $C_1$-$C_6$alkyl, unsubstituted or substituted with one or more of a substituent $S^3$; phenyl, unsubstituted or substituted with one or more of a substituent $S^3$; or a 3-6 membered heterocyclyl group containing one or more than one heteroatom selected from nitrogen, sulfur and oxygen, which heterocyclyl group may furthermore optionally be fused to a phenyl ring or a 5-6 membered heterocyclic ring and which whole group is unsubstituted or substituted with one or more of a substituent $S^3$, wherein each $S^3$ independently of other substituents $S^3$ represents unsubstituted $C_1$-$C_6$alkyl, unsubstituted phenyl or an unsubstituted 5-6 membered heterocyclic ring; $C_1$-$C_6$alkoxy, hydroxyl, carboxy, amino, $C_1$-$C_6$alkyl amino, di($C_1$-$C_6$)alkyl amino, cyano, halogen, or a group of formula —NH—CO—$NH_2$, —CO—$NH_2$, —NH—CH=NH, —NH—CO—$NH_2$, —NH—$SO_2$—$NH_2$ or —NH—(C=NH)—$NH_2$; or $R^3$ and $R^4$ together form a $C_3$-$C_7$polymethylene group, which is unsubstituted or substituted with one or more of a substituent $S^3$, wherein each $S^3$ has independently of other substituents $S^3$ one of the meanings defined above.

The term "$C_1$-$C_6$alkyl" and "—($C_{1n}H_{2n}$)—", as used in the present application, refers to branched or, preferably, straightchain $C_1$-$C_6$alkyl or —($C_{1n}H_{2n}$)—, wherein n is an integer from 1 to 6, preferably from 1 to 4, such as in particular methyl, ethyl, propyl, butyl, pentyl, hexyl, isopropyl, isobutyl, tert-butyl or neopentyl. Preferred are $C_1$-$C_4$alkyl groups. The term "$C_1$-$C_6$alkoxy" means an alkoxy group based on a $C_1$-$C_6$alkyl according to the above definition.

The term "$C_3$-$C_7$polymethylene group" refers to a group of formula —$(CH_2)_{3-7}$— which may comprise one or two double bonds and which may be unsubstituted or substituted as specified.

The terms "heterocyclyl group" and "heterocyclic ring" refer to corresponding groups which are saturated or unsaturated.

The term "a 3-6 membered heterocyclyl group containing one or more than one heteroatom selected from nitrogen, sulfur and oxygen, which heterocyclyl group may furthermore optionally be fused to a phenyl ring or a 5-6 membered heterocyclic ring" refers e.g. to azetidin, thiophen, benzothiophen, furan, pyran, benzofuran, isobenzofuran, pyrrol, imidazole, pyrazole, pyridin, pyrazin, pyrimidin, pyridazin, indazolin, indol, isoindol, indazol, purin, oxazol, isooxazol, furazan, pyrrolidin, pyrrolin, imidazolidin, piperidin, piperazin, thiazol, isothiazol, thiazepine or hydrothiazepin. Many other suitable heterocyclic groups for the purposes of the invention are known to the skilled persons and/or can be readily found in the literature. Preferred are 5-6 membered heterocyclic groups containing one or more than one heteroatom selected from nitrogen, sulfur and oxygen, in particular nitrogen and sulphur, which heterocyclyl group may furthermore optionally be fused to a phenyl ring or a 5-6 membered heterocyclic ring containing one or more than one heteroatom selected from nitrogen, sulfur and oxygen, in particular nitrogen and sulphur.

"Substituted by one or more than one" means preferably "substituted by one or two", e.g. "substituted by one".

More preferably $R^5$ represents halogen, cyano, $C_1$-$C_6$alkoxy, amino, ($C_1$-$C_6$alkyl)amino, di($C_1$-$C_6$alkyl) amino, or a group of formula —CO—$R^6$, —NH—CO—$R^6$— CO—$NH_2$, —NH—CO—$NH_2$, —NH—$SO_2$—$NH_2$ or —NH—(C=NH)—$NH_2$, wherein $R^6$ represents $C_1$-$C_6$alkyl, phenyl or a 5-6 membered heterocyclic ring and may be unsubstituted or substituted with one or more of a substituent selected from one of the substituents $S^3$ as defined above.

The term halogen refers to fluorine, chlorine, bromine and iodine, preferably fluorine and chlorine.

Another group of particularly preferred compounds of formula (II) are the compounds, wherein $R^4$ represents a group of formula —$(S)_m$—$R^7$, m is 0 or 1 and $R^7$ represents a 3-6 membered heterocyclic group containing one or more than one heteroatom selected from nitrogen, sulfur and oxygen, which heterocyclyl group may furthermore optionally be fused to a phenyl ring or a 5-6 membered heterocyclic ring and which whole group is unsubstituted or substituted as defined in detail above. Even more preferred are such compounds of formula (II), when m is 1.

Also preferred are the compounds of formula (II), wherein
$R^1$ represents hydrogen or $C_1$-$C_6$alkyl;
$R^2$ represents hydrogen or $C_1$-$C_6$alkyl; and
$R^3$ represents $C_1$-$C_6$alkyl;
in particular, when one of $R^1$ and $R^2$ represents hydrogen and the other —$CH_3$ and $R^3$ is —$CH_3$.

The compounds of formula (III),

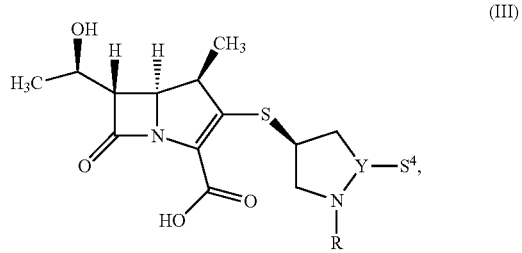

(III)

wherein
Y represents nitrogen or >CH—;
$S^4$ represents hydrogen or has the meaning of $S^1$ as defined above; and
R represents hydrogen; $C_1$-$C_4$alkyl, in particular methyl, or —(N=H)—$C_1$-$C_4$alkyl, in particular —(N=H)—$CH_3$, or
$S^4$ and R together the nitrogen atom or group Y to which they are bound form a 5-6 membered heterocyclic ring;
R being most preferably hydrogen or methyl,
or pharmaceutically acceptable salts thereof,
form another group of embodiments of a carbapenem which is particularly preferred for the purposes of the present invention.

The following carbapenem antibiotics or their pharmaceutically acceptable salts are specifically preferred examples useful in the present invention:

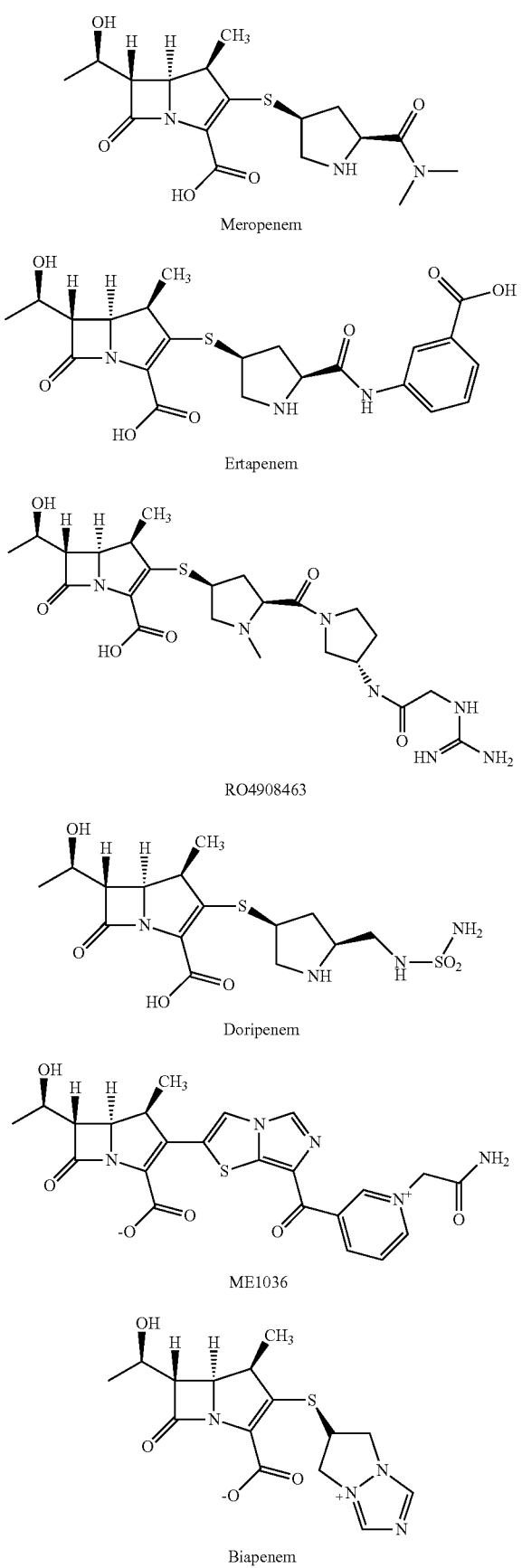
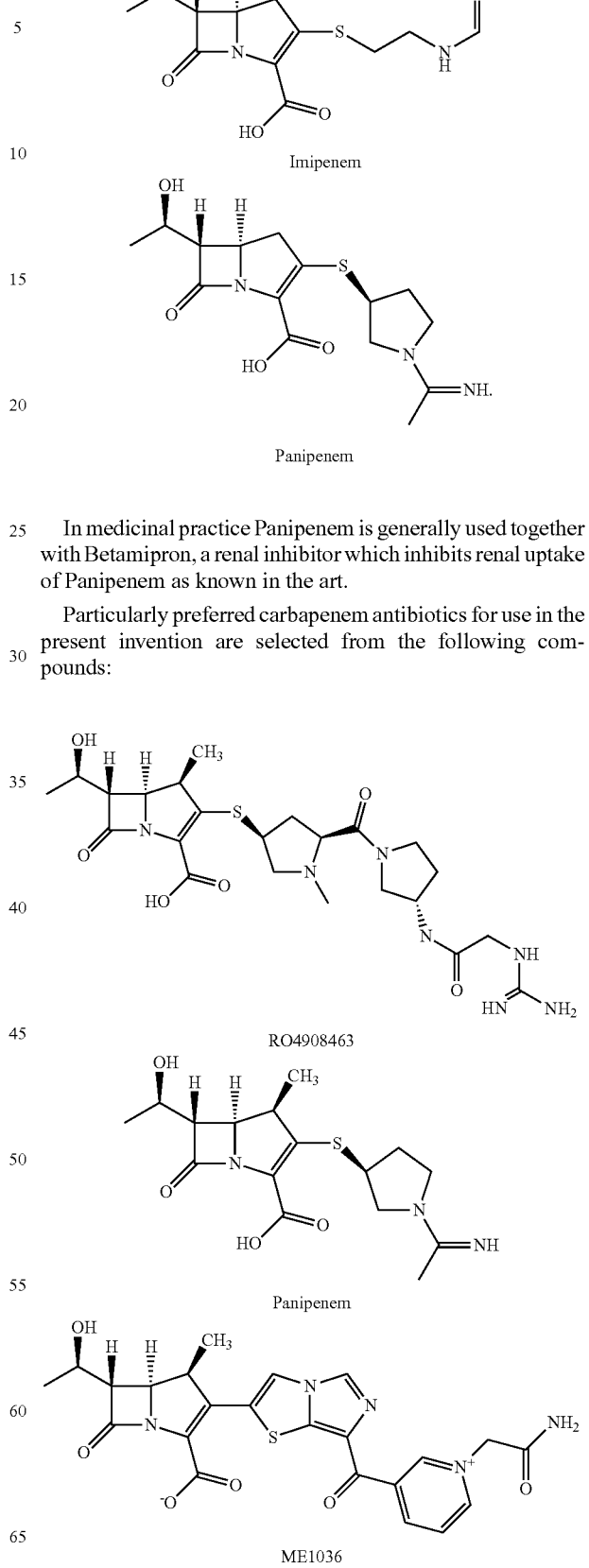
In medicinal practice Panipenem is generally used together with Betamipron, a renal inhibitor which inhibits renal uptake of Panipenem as known in the art.
Particularly preferred carbapenem antibiotics for use in the present invention are selected from the following compounds:

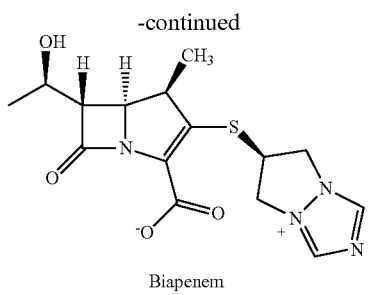
Biapenem or a pharmaceutically acceptable salt thereof.

A further preferred subject of the present invention is the use of the monobactam antibiotic of formula (I) as described above or a pharmaceutically acceptable salt thereof for the manufacture of a medicament for the treatment of a bacterial infection in combination with Imipenem or a pharmaceutically acceptable salt thereof. In medicinal practice Imipenem is generally used together with Cilastin, an inhibitor of the renal dipeptidase in the proximal tubulus of the kidney, which is used in order to stabilize Imipenem against inactivation, similar as the Betamipron in combination with Panipenem as mentioned above.

Another preferred subject of the present invention is use of the monobactam antibiotic of formula (I) as described above or a pharmaceutically acceptable salt thereof for the manufacture of a medicament for the treatment of a bacterial infection in combination with Meropenem or a pharmaceutically acceptable salt thereof. Meropenem is sometimes also used together with Cilastin similar to Imipenem (Antimicrob. Agents Chemother. 2000, 44, 885-890).

Another preferred subject of the present invention is use of the monobactam antibiotic of formula (I) as described above or a pharmaceutically acceptable salt thereof for the manufacture of a medicament for the treatment of a bacterial infection in combination with Ertapenem or a pharmaceutically acceptable salt thereof.

Yet another preferred subject of the present invention is use of the monobactam antibiotic of formula (I) as described above or a pharmaceutically acceptable salt thereof for the manufacture of a medicament for the treatment of a bacterial infection in combination with Doripenem or a pharmaceutically acceptable salt thereof.

The compound of formula (I) or the pharmaceutically acceptable salts thereof can be administered according to the invention before, simultaneously with or after the administration of the carbapenem antibiotic or the pharmaceutically acceptable salt thereof. Substantially simultaneous or an exactly simultaneous administration of the combination partners is generally preferred.

The compounds of formula (I) or pharmaceutically acceptable salts thereof and the carbapenem antibiotics or pharmaceutically acceptable salts thereof can be administered by any route of administration, preferably in the form of a pharmaceutical composition adapted to such route. Dosage and route of administration should be determined by susceptibility of the causative organisms, severity and site of infection, and the specific condition of the patient and be selected accordingly. Preferred types of pharmaceutical compositions are, for example, administered orally, by inhalation or more preferably parenterally e.g. intravenously or intramuscularly.

Formulations for parenteral administration include but are not limited to the form of aqueous isotonic sterile injections, solutions, concentrates or solutions for further dilutions (e.g. for infusions), or suspensions, including nanosuspensions and nanocrystals. These solutions or suspensions can be prepared from sterile powders, granules or lyophilizates. The compounds can be dissolved in sterile water or in various sterile buffers that may contain, but are not limited to contain, sodium chloride, polyethylene glycol, propylene glycol, ethanol, sucrose, glucose, arginine, lysine, citric acid, lactic acid phosphoric acid and corresponding salts. The formulation can contain from 0.1% to 99% by weight, preferably 10%-90% by weight, of each of the active ingredients. If the compositions contain dosage units, each unit preferably contains from 50 mg to 4 g of each active substance.

A further subject of the present invention is accordingly a pharmaceutical product comprising the compound of formula (I) or a pharmaceutically acceptable salt thereof and a carbapenem antibiotic or a pharmaceutically acceptable salt thereof.

A pharmaceutical product according to the invention can e.g. comprise one or more than one dosage unit of a compound of formula (I) or a pharmaceutically acceptable salt thereof and one or more than one other dosage unit containing a carbapenem antibiotic or a pharmaceutically acceptable salt thereof and being free of the compound of formula (I). By the way of example, a pharmaceutical product of the invention may comprise two separate packages, each of them comprising a pharmaceutical formulation comprising just one of the combination partners in an appropriate dosage form.

Another embodiment of the pharmaceutical product according to the invention comprises one or more than one dosage unit, and each dosage unit comprises both, the compound of formula (I) or a pharmaceutically acceptable salt thereof and a carbapenem antibiotic or a pharmaceutically acceptable salt thereof. Such a fixed dose combination generally comprises the compound of formula (I) or the pharmaceutically acceptable salt thereof and the carbapenem antibiotic or the pharmaceutically acceptable salt thereof as well as a pharmaceutically acceptable carrier and optionally appropriate further excipients as typical for the respective dosage form.

The pharmaceutical products according to the present invention comprise the compound of formula (I) or the pharmaceutically acceptable salt thereof and the carbapenem antibiotic or the pharmaceutically acceptable salt thereof in an appropriate weight ratio, e.g. in a weight ratio of 10:1 to 1:10, preferably from 5:1 to 1:5, more preferably from 3:1 to 1:3 like e.g. from 2:1 to 1:2 or about 1:1.

The pharmaceutical products according to the present invention are active against a variety of bacterial organisms, in particular against Gram-positive bacteria including for example *Staphylococcus aureus, Staphylococccus epidermidis, Enterococcus faecalis, Streptococcus pneumonia* and Gram-negative bacteria, including Enterobacteriaceae, for example *Escherichia coli, Enterobacter cloacae, Enterobacter aerogenes, Citrobacter freundii, Klebsiella pneumoniae, Klebsiella oxytoca, Proteus vulgaris, Providencia rettgeri; Pseudomonas* for example *P. aeruginosa; Acinetobacter* for example *A. baumannii; Burkholderia*, for example *B. cepacea; B. mallei; B. pseudomallei; Stenotrophomonas* for example *S. maltophilia; Haemophilus influenzae.*

The products can thus be used for treatment of infectious diseases including e.g. nosocomial pneumonia, community-acquired pneumonia, urinary tract infection, complicated intra-abdominal infection, complicated skin/skin structure infection, cystic fibrosis, sepsis.

The dosage of the compound of formula I and of the pharmaceutically compatible salts thereof and the carbapenem antibiotics or salts thereof for said treatment can vary within wide limits and will be fitted in each particular case to the individual requirements of the patient to be treated and to the pathogens to be controlled. In general, a dosage of about 0.1 to about 4 g, e.g. about 0.5 to about 2 g, of total antibiotic administered one to four times over a 24 hours period should be appropriate.

The present invention is further illustrated by the following non-limiting examples.

EXAMPLE 1

Preparation of (3S)-3-{(2Z)-2-(2-amino(1,3-thiazol-4-yl))-3-[(1,5-dihydroxy-4-oxo(2-hydropyridyl)) methoxy]-3-azaprop-2-enoylamino}-4,4-dimethyl-2-oxoazetidinyl hydroxysulfonate (Compound of Formula (I))

The monobactam antibiotic I is prepared according to the synthesis outlined in Scheme 4 and according to the procedures described below.

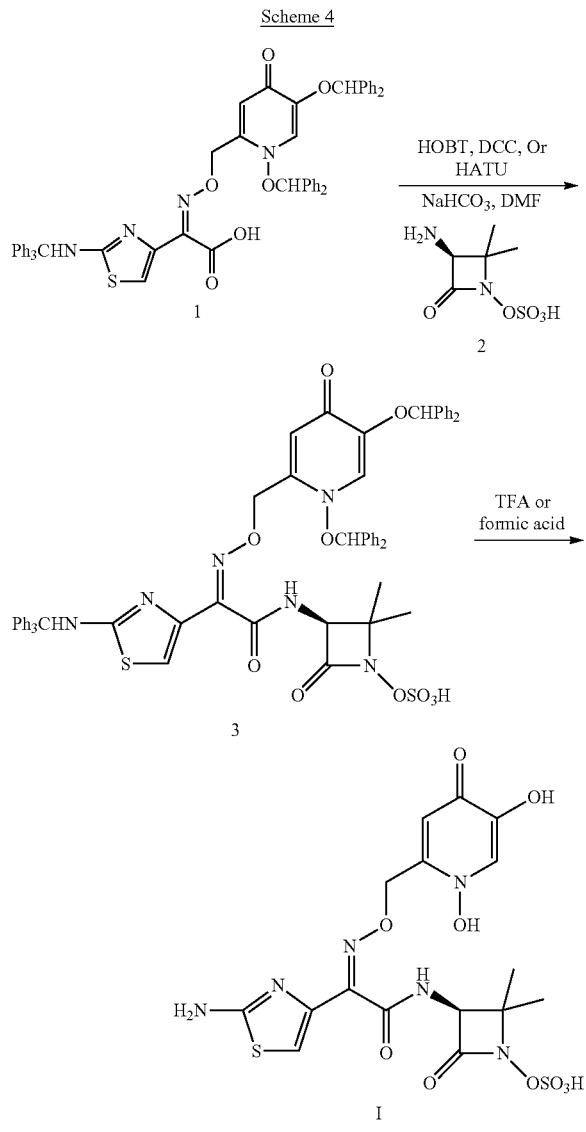

Preparation of (3S)-3-{(2Z)-3-{[1,5-bis(diphenyl-methoxy)-4-oxo(2-hydropyridyl)]methoxy}-2-{2-[(triphenylmethyl)amino](1,3-thiazol-4-yl)}-3-azaprop-2-enoylamino}-4,4-dimethyl-2-oxoazetidinyl hydroxysulfonate (3)

Using HOBt as Coupling Reagent (2Z)-3-{[1,5-Bis(diphenylmethoxy)-4-oxo(2-hydropyridyl)]-methoxy}-2-{2-[(triphenylmethyl)amino](1,3-thiazol-4-yl)}-3-azaprop-2-enoic acid 1 (0.89 g, 0.95 mmol, J. Antibiotics 1990, 1450 and WO-A-02/22613), hydroxybenzotriazol (HOBT) (0.14 g, 1.03 mmol) and dicyclohexylcarbodiimide (0.26 g, 1.41 mmol) are dissolved in DMF (25 mL) at room temperature. First, (3S)-3-Amino-4,4-dimethyl-2-oxoazetidinyl hydroxysulfonate 2 (0.20 g, 0.95 mmol, J. Org. Chem. 2003, 177 and Tetrahedron Lett. 1986, 2786) and then 30 min later NaHCO$_3$ (0.09 g, 1.05 mmol) are added to the previous solution. The resulting mixture is stirred for 18 h. The precipitate formed is filtrated and ethyl acetate is added to the filtrate. The organic phase is washed twice with an aqueous solution saturated with NaCl, dried over Na SO$_4$ and the solvents are evaporated in vacuo. The residue is triturated in ethyl acetate (30 mL) to afford 0.5 g of the desired compound 3 as white solid after filtration.

HPLC purity: 98%.

Using HATU as Coupling Reagent

A solution of DMSO (10 mL) containing HATU (1.38 g, 3.64 mmol) is added at room temperature to a suspension of (2Z)-3-{[1,5-Bis(diphenylmethoxy)-4-oxo(2-hydropyridyl)]methoxy}-2-{2-[(triphenylmethyl)amino](1,3-thiazol-4-yl)}-3-azaprop-2-enoic acid 1 (3.0 g, 3.16 mmol, J. Antibiotics 1990, 1450 and WO-A-02/22613) and (3S)-3-mino-4,4-dimethyl-2-oxoazetidinyl hydroxysulfonate 2 (1.18 g, 5.06 mmol, J. Org. Chem. 2003, 177 and Tetrahedron Lett. 1986, 2786) in DMSO (20 mL). Then NaHCO$_3$ (0.81 g, 9.65 mmol) is added as solid. The resulting mixture, which becomes a solution after 1 h, is stirred for 24 h at room temperature. Ethyl acetate (50 mL) is then added and the resulting solution is washed 6 times with brine (6×30 mL). The organic phase dried over Na SO$_4$ and the mixture is concentrated by evaporation of the solvent in vacuo until about 25 mL of solution remain in the flask. At room temperature, cyclohexane (40 mL) is added dropwise to the yellow solution. The resulting precipitate is collected by filtration and the cake is then washed with cyclohexane (2×5 mL) to give 3.3 g of the desired compound 3.

HPLC purity: 95%.

Both methods give a product with the same NMR and MS spectra.

$^1$H-NMR (DMSO-d$_6$) δ: 1.05 (s, 3H), 1.34 (s, 3H), 4.49 (d, 1H, J=7.8 Hz), 4.62 (m, 2H), 6.12 (s, 1H), 6.33 (s, 1H), 6.39 (s, 1H), 6.72 (s, 1H), 7.20-7.43 (m, 35H), 7.72 (s, 1H), 8.83 (1, 1H), 9.52 (d, 1H, J=7.8 Hz).

Preparation of (3S)-3-{(2Z)-2-(2-amino(1,3-thiazol-4-yl))-3-[(1,5-dihydroxy-4-oxo(2-hydropyridyl)) methoxy]-3-azaprop-2-enoylamino}-4,4-dimethyl-2-oxoazetidinyl hydroxysulfonate (I)

(a) Using Trifluoroacetic Acid (3S)-3-{(2Z)-3-{[1,5-Bis(diphenylmethoxy)-4-oxo(2-hydropyridyl)]methoxy}-2-{2-[(triphenylmethyl)amino](1,3-thiazol-4-yl)}-3-azaprop-2-enoylamino}-4,4-dimethyl-2-oxoazetidinyl hydroxysulfonate 3 (0.25 g, 0.23 mmol) and triethylsilane (0.08 g, 0.69 mmol) are dissolved in dichloromethane (15 mL) and cooled at −10° C. Then trifluoroacetic acid (1.04 g, 9.2 mmol) is slowly added to the cooled mixture.

The temperature is slowly raised to 25° C. and the reaction is stirred for an additional 4 h. The solvent is removed in vacuo and the residue was triturated with a solvent mixture containing hexane and ethyl acetate (1:4) to give 0.11 g of the desired compound I as a solid.

HPLC purity: 94%.

(b) Using Formic Acid

In formic acid (3 mL) at 5° C., (3S)-3-{(2Z)-3-{[1,5-Bis(diphenylmethoxy)-4-oxo(2-hydropyridyl)]methoxy}-2-{2-[(triphenylmethyl)amino](1,3-thiazol-4-yl)}-3-azaprop-2-enoylamino}-4,4-dimethyl-2-oxoazetidinyl hydroxysulfonate 3 (0.40 g, 0.31 mmol) is added and the clear solution is stirred for 5 h at 5-10° C. Then ethyl acetate (40 mL) is added and the resulting precipitate is filtrated off. The white precipitate is washed with additional ethyl acetate (2×5 mL) and give after drying under vacuum 0.09 g of the desired compound I HPLC purity: 92%.

Both methods give a product with the same NMR and MS spectra.

$^1$H-NMR (DMSO-$d_6$) δ: 1.22 (s, 3H), 1.42 (s, 3H), 4.63 (d, 1H, J=7.7 Hz), 5.28 (s, 2H), 6.81 (s, 1H), 7.13 (s, 1H), 7.27 (br s, 2H), 8.19 (s, 1H), 9.59 (d, 1H, J=7.7 Hz).

-ESI-MS spectrum: m/z: 517 [M-H]$^+$.

According to the methods described above, the compound of formula (I) is generally obtained in an amorphous form. Although it may be used in said form it may optionally be converted into crystalline material, e.g. as described herein below.

Crystallisation Procedure for Compound of Formula I

The crude material of compound of formula I previously prepared (1.31 g) is suspended in acetonitrile (15 mL) at room temperature. Then water (3.30 mL) is added to the previous suspension. The clear solution (if solution is not clear, the suspension could be gently warmed) is stirred at room temperature for a few minutes until the crystallisation started. The suspension is stirred for 1 h at room temperature and an additional hour at 0° C. After filtration, 1.05 g of compound of formula I is obtained as white crystalline material, which has the same NMR and MS spectra as reported previously for amorphous material.

The crystalline material is characterized by an infrared spectrum as listed in the following table (FTIR recorded with powder at a resolution of 2 cm$^{-1}$, collecting 16 scans from 4000 to 500 cm$^{-1}$, Bruker Vector 22 spectrometer with ATR Golden gate).

FTIR spectrum of crystalline material of the compound of formula (I):

| Wavenumber (cm$^{-1}$) |
| --- |
| 3102.51 |
| 2739.68 |
| 1766.15 |
| 1634.10 |
| 1587.99 |
| 1527.49 |
| 1449.58 |
| 1357.88 |
| 1335.03 |
| 1286.46 |
| 1239.18 |
| 1204.65 |

-continued

| Wavenumber (cm$^{-1}$) |
| --- |
| 1165.49 |
| 1129.59 |
| 1044.69 |
| 1021.99 |
| 1010.65 |
| 941.13 |
| 907.87 |
| 861.18 |
| 823.99 |
| 802.53 |
| 712.18 |
| 678.48 |
| 628.91 |
| 583.63 |
| 569.68 |
| 550.26 |
| 536.37 |
| 525.52 |
| 515.44 |

The crystalline material exhibits an X-Ray Power Diffraction ("XRPD") pattern obtained using CuKa radiation as shown in the following Table and in FIG. 1.

| XRPD Diagram | |
| --- | --- |
| 2θ angle (°) | Rel. Intensity % |
| 6.86 | 64 |
| 7.19 | 3 |
| 10.73 | 7 |
| 10.97 | 5 |
| 13.32 | 27 |
| 13.72 | 28 |
| 15.11 | 69 |
| 15.57 | 100 |
| 17.41 | 29 |
| 17.68 | 13 |
| 17.88 | 20 |
| 18.78 | 15 |
| 18.95 | 14 |
| 19.34 | 16 |
| 19.76 | 4 |
| 20.38 | 8 |
| 20.66 | 16 |
| 20.86 | 15 |
| 21.55 | 3 |
| 22.27 | 10 |
| 22.84 | 31 |
| 23.45 | 18 |
| 23.62 | 19 |
| 23.97 | 16 |
| 24.49 | 22 |
| 24.87 | 16 |
| 25.37 | 52 |
| 26.32 | 36 |
| 27.08 | 34 |
| 27.74 | 12 |
| 28.38 | 33 |
| 28.74 | 32 |
| 29.17 | 11 |
| 29.97 | 10 |
| 30.53 | 12 |
| 31.00 | 23 |
| 32.47 | 2 |
| 33.27 | 17 |
| 34.47 | 5 |
| 36.12 | 3 |
| 37.04 | 9 |
| 37.44 | 6 |
| 37.98 | 12 |
| 38.19 | 12 |
| 38.68 | 9 |

-continued

| XRPD Diagram | |
|---|---|
| 2θ angle (°) | Rel. Intensity % |
| 39.30 | 5 |
| 39.75 | 7 |

The 2θ angles have an error of about ±0.1°. It is known that the values for the relative Intensity of the peaks are more strongly dependent from certain properties of the measured sample than the line position, e.g. from the size of the crystals and their orientation in the sample. Variations of ±20% of the shown peak intensities are therefore likely to occur.

The crystalline material is furthermore characterized by Thermal Gravimetric Analysis ("TGA") data as indicated in the Table below and obtained using a scan rate of 10 deg/min (Perkin-Elmer TGS2). The weight loss of the material is about 7% when the temperature of the material is raised from room temperature to 100° C. A further weight loss is observed at 192-193° C. corresponding to the melting/decomposition temperature of the sample.

| Temperature [° C.] | Weight loss [%] |
|---|---|
| 25 | 1.12 |
| 50 | 4.46 |
| 75 | 5.70 |
| 100 | 8.05 |
| 125 | 8.09 |
| 150 | 8.14 |
| 175 | 8.29 |
| 200 | 55.60 |
| 225 | 56.10 |
| 250 | 56.31 |
| 275 | 56.52 |
| 300 | 56.75 |
| 325 | 57.06 |
| 350 | 57.55 |
| 375 | 58.35 |
| 400 | 29.54 |
| 425 | 60.99 |
| 450 | 62.51 |
| 475 | 63.95 |
| 500 | 65.30 |

EXAMPLE 2

(a) Preparation of the Sodium Salt of Compound of Formula I

Sodium hydrogen carbonate (0.0077 g, 0.095 mmol) is added portionwise to a water solution (20 mL) cooled at 5° C. containing compound of formula I (0.05 g, 0.1 mmol) (pH 2-3). The clear solution is stirred for 15 minutes at 5° C. (pH 5-6). The solution is frozen and lyophilized over the night to give 0.052 g of a white solid.

$^1$H-NMR (DMSO-$d_6$) δ: 1.24 (s, 3H), 1.45 (s, 3H), 4.65 (d, 1H, J=7.7 Hz), 5.20 (s, 2H), 6.82 (s, 1H), 6.90 (s, 1H), 7.26 (br s, 2H), 7.95 (s, 1H), 9.60 (d, 1H, J=7.7 Hz).

(b) Preparation of the L-Arginine Salt of Compound of Formula I

Compound of formula I (0.20 g, 0.39 mmol) and L-arginine (0.0672 g, 0.39 mmol) are vigorously mixed as solid together at room temperature. The resulting powder is dissolved in water (40 mL) and stirred for 2-3 min at room temperature. The solution is frozen and lyophilized over the night to give 0.260 g of a white solid.

$^1$H-NMR (DMSO-$d_6$) δ: 1.24 (s, 3H), 1.44 (s, 3H), 1.50-1.80 (m, 4H), 3.11 (br m, 2H), 3.53 (br m, 1H), 4.65 (d, 1H, J=7.7 Hz), 5.10 (s, 2H), 6.72 (s, 1H), 6.80 (s, 1H), 7.22 (br s, 2H), 7.72 (s, 1H), 8.13 (br s, 1H), 9.60 (d, 1H, J=7.7 Hz).

(c) Preparation of the L-Lysine Salt of Compound of Formula I

Compound of formula I (0.20 g, 0.39 mmol) and L-lysine (0.0564 g, 0.39 mmol) are vigorously mixed as solid together at room temperature. The resulting powder is dissolved in water (45 mL) and stirred for 2-3 min at room temperature. The solution is frozen and lyophilized over the night to give 0.250 g of a white solid.

$^1$H-NMR (DMSO-$d_6$) δ: 1.24 (s, 3H), 1.30-1.80 (m, 9H), 2.77 (br m, 2H), 3.50 (br m, 1H), 4.66 (d, 1H, J=7.7 Hz), 5.11 (s, 2H), 6.73 (s, 1H), 6.79 (s, 1H), 7.22 (br s, 2H), 7.73 (s, 1H), 9.61 (d, 1H, J=7.7 Hz).

EXAMPLE 3

Antimicrobial activity of the compounds and of their combinations is determined against a selection of organisms according to standard procedures described by the National Committee for Clinical Laboratory Standards (NCCLS document M7-A6). The compounds are dissolved in 100% DMSO or sterile broth according to their aqueous solubility and are diluted to the final reaction concentration (0.06-32 μg/mL) in microbial growth media (IsoSensiTest Broth+16 μg/mL 2,2'-bipyridyl). In all cases the final concentration of DMSO incubated with the bacteria is less than or equal to 1%. For estimation of the minimal inhibitory concentrations (MIC), 2-fold dilutions of compounds are added to wells of a microtitre plate containing $10^6$ bacteria/mL. Plates are incubated overnight at an appropriate temperature (30° C. or 37° C.) and optical densities assessed by eye. The MIC value is defined as the lowest compound concentration completely inhibiting visible growth of the test organism. Synergism tests are performed under the same conditions as described above but with two antimicrobial agents dispensed in checkerboard format [Isenberg H D (1992) Synergism testing: Broth microdilution checkerboard and broth macrodilution methods. In: Clinical Microbiology Procedures Manual vol. 1. Washington, D.C.: American Society for Microbiology. Sections 5.18.1 to 5.18.28.]. The strains used are: *Pseudomonas aeruginosa* 6067 (Accession number at the DSMZDeutsche Sammlung von Mikroorganismen und Zellkulturen GmbH, Inhoffenstr. 7 B, D-38124 Braunschweig: DSM 18987), *Pseudomonas aeruginosa* (67/2B)₂R.A. (DSM 18988), *Achromobacter* (formerly *Alcaligenes*) xylosoxidans QK3/96 (DSM 18991), *Enterobacter aerogenes* Zayakosky 5 (DSM 18992).

Aztreonam as well as compound A and compound B, the latter both disclosed in WO 98/47895, which are structurally similar to the compound of formula I are used as comparators.

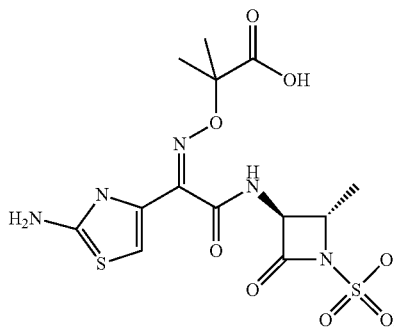

Aztreonam

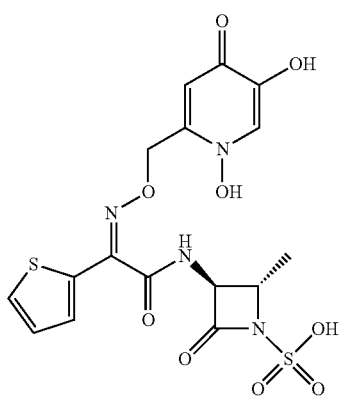

Compound A

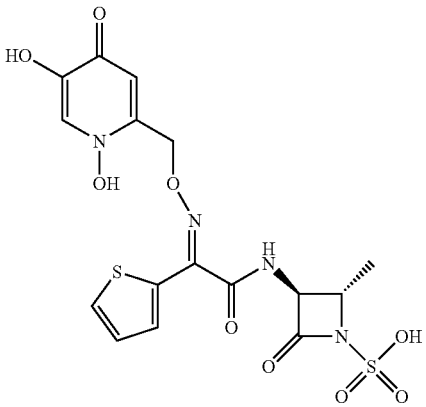

Compound B

Table 1 shows that combining of equal weights of the monobactam antibiotic of formula (I) according to the present invention and carbapenems of formula II lowers the MIC of the carbapenem against carbapenem-resistant strains by an amount that is more than expected from the combination of two active compounds. The MIC of the combinations according to the invention is also less than the MIC of a similar equigravimetric combination of aztreonam and the corresponding carbapenems. Finally, it is shown that the combinations of the present invention exhibit lower MIC values than combinations according to WO 98/47895, e.g. WO 98/47895, Example 1, which corresponds to Compound A referred to in Table 1.

TABLE 1

Minimum Inhibitory Concentrations (mg/L) of representative Combinations between Monobactam Antibiotics and Carbapenems

| | Minimum Inhibitory Concentration (mg/L) | | | |
|---|---|---|---|---|
| Substance/combination | P. aeruginosa 6067 [DSM 18987] | A. xylosoxidans QK3/96 [DSM 18991] | E. aerogenes Zayakosky 5 [DSM 18992] | P. aeruginosa (67/2B)2R.A. [DSM 18988] |
| Compound of formula I* | 16 | 16 | 16 | 32 |
| Aztreonam | 16 | >64 | 64 | 4 |
| Compound A | >64 | >64 | >64 | >64 |
| Compound B | >64 | >64 | >64 | >64 |
| Meropenem | 16 | 16 | 16 | 4 |
| Meropenem + Compound of formula I* | 4 | 8 | 8 | 2 |
| Meropenem + aztreonam | 16 | 16 | 16 | 8 |
| Meropenem + Compound A | 16 | 16 | 16 | 8 |
| Meropenem + Compound B | 16 | 16 | 16 | 8 |
| Imipenem | 4 | 4 | 32 | 16 |
| Imipenem + Compound of formula I* | 2 | 4 | 16 | 8 |
| Imipenem + aztreonam | 4 | 32 | 32 | 16 |
| Imipenem + Compound A | 4 | 32 | 32 | 16 |
| Imipenem + Compound B | 4 | 32 | 32 | 16 |
| Ertapenem | >32 | >32 | >32 | >32 |
| Ertapenem + Compound of formula I* | 16 | 8 | 16 | 8 |
| Doripenem | 16 | 16 | 8 | 4 |
| Doripenem + Compound of formula I* | 8 | 8 | 4 | 4 |

*of present application

Fractional inhibitory concentrations (FIC) are determined according to the formula:

$$FIC = \frac{MIC \text{ of drug } A \text{ in combination}}{MIC \text{ of drug } A \text{ alone}} + \frac{MIC \text{ of drug } B \text{ in combination}}{MIC \text{ of drug } B \text{ alone}}$$

[Isenberg HD (1992); Eliopoulos, G. M. & Moellering, R. C. (1996). In *Antibiotics in Laboratory Medicine*, 4th edn, (Lorian, V., Ed.), pp. 330-96. Williams and Wilkins, Baltimore, Md.].

Table 2 shows the interaction between compound of formula I, or the reference compounds Aztreonam, compound A and compound B, and carbapenems using the checkerboard titration method. Additive or synergistic interactions are only observed between the compound of formula I and carbapenem antibiotics. Under the same conditions, combinations with Aztreonam, compound A or compound B show indifference or even antagonism.

The interpretation of the FIC values is according to the definitions given by Sader H S, Huynh H K, Jones R N; Contemporary in vitro synergy rates for aztreonam combined with newer fluoroquinolones and β-lactams tested against Gram-negative bacilli; Diagn. Microbiol. Infect. Dis. 47 (2003) 547-550, namely as follows:

S=FIC≤0.5: synergism
s=0.5<FIC<1: partial synergism
D=FIC=1: additive effect
I=1<FIC<4: indifferent
N=4≤FIC: antagonism

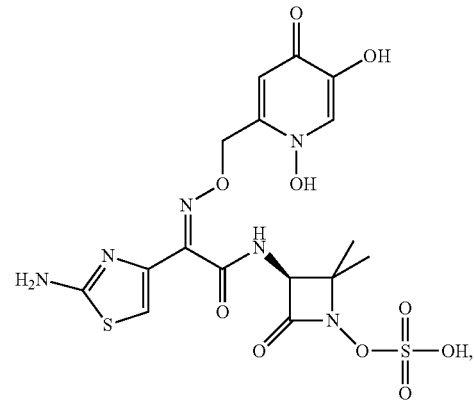

wherein the oxyimino moiety has the Z-orientation, or a pharmaceutically acceptable salt thereof and at least one carbapenem antibiotic, selected from the group consisting of Meropenem, Imipenem, Ertapenem, Doripenem or pharmaceutically acceptable salts thereof.

2. The pharmaceutical product of claim 1, comprising at least one dosage unit comprising the compound of formula (I) or a pharmaceutically acceptable salt thereof and at least one dosage unit comprising a carbapenem antibiotic, selected from the group consisting of Meropenem, Imipenem, Ertapenem, Doripenem or a pharmaceutically acceptable salt thereof.

3. The pharmaceutical product of claim 1, comprising at least one dosage unit, each of said dosage units comprising both, a monobactam antibiotic of formula (I)

TABLE 2

Fractional Inhibitory Concentrations (FIC) Observed for Representative Combinations between Monobactam Antibiotics and Carbapenems

| Substance/combination | A. xylosoxidans QK3/96 | E. aerogenes Zayakosky 5 | P. aeruginosa (67/2B)2R.A. | P. aeruginosa 6067 |
|---|---|---|---|---|
| Meropenem + Compound of formula I | 0.51 (s) | 0.48 (S) | 0.62 (s) | 0.72 (s) |
| Meropenem + Aztreonam | 1.8 (I) | 1.3 (I) | 1.1 (I) | 1.1 (I) |
| Meropenem + Compound A | 2.1 (I) | 1.8 (I) | 3.3 (I) | 2.2 (I) |
| Meropenem + Compound B | 2.0 (I) | 1.7 (I) | 3.3 (I) | 3.3 (I) |
| Imipenem + Compound of formula I | 0.78 (s) | 0.69 (s) | 1.0 (D) | 0.62 (s) |
| Imipenem + Aztreonam | 9.0 (N) | 2.1 (I) | 1.8 (I) | 2.2 (I) |
| Imipenem + Compound A | 5.8 (N) | 2.4 (I) | 2.8 (I) | 14 (N) |
| Imipenem + Compound B | 9.9 (N) | 2.6 (I) | 2.7 (I) | 13 (N) |
| Ertapenem + Compound of formula I | 0.7 (s) | 0.85 (s) | 0.65 (s) | 2.0 (I) |
| Doripenem + Compound of formula I | 0.37 (S) | 0.43 (S) | 1.2 (I) | 1.0 (D) |
| Doripenem + Compound A | 3.1 (I) | 3.1 (I) | 7.3 (N) | 2.4 (I) |
| Doripenem + Compound B | 2.3 (I) | 1.9 (I) | 4.6 (N) | 2.4 (I) |

We claim:

1. A pharmaceutical product comprising a monobactam antibiotic having the oxyimino moiety >C=N—O—, said antibiotic having the formula (I)

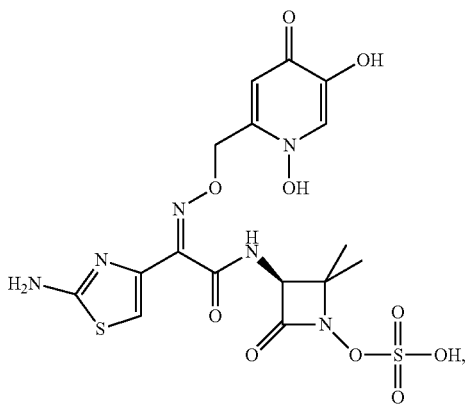

(I)

or a pharmaceutically acceptable salt thereof and at least one carbapenem antibiotic, selected from the group consisting of Meropenem, Imipenem, Ertapenem, Doripenem or a pharmaceutically acceptable salt thereof.

4. The pharmaceutical product of claim 2, wherein the carbapenem antibiotic is Imipenem or a pharmaceutically acceptable salt thereof.

5. The pharmaceutical product of claim 2, wherein the carbapenem antibiotic is Meropenem or a pharmaceutically acceptable salt thereof.

6. The pharmaceutical product of claim 2, wherein the carbapenem antibiotic is Ertapenem or a pharmaceutically acceptable salt thereof.

7. The pharmaceutical product of claim 2, wherein the carbapenem antibiotic is Doripenem or a pharmaceutically acceptable salt thereof.

8. The pharmaceutical product of claim 1, comprising the monobactam antibiotic of formula (I) or the pharmaceutically acceptable salt thereof and the carbapenem antibiotic or the pharmaceutically acceptable salt thereof in a weight ratio of 10:1 to 1:10.

9. The pharmaceutical product of claim 8, wherein the weight ratio of the monobactam antibiotic of formula (I) or the pharmaceutically acceptable salt thereof and the carbapenem antibiotic or the pharmaceutically acceptable salt thereof is from 3:1 to 1:3.

10. The pharmaceutical product of claim 1, which is a composition comprising the monobactam antibiotic of formula (I) or the pharmaceutically acceptable salt thereof and the carbapenem antibiotic or a pharmaceutically acceptable salt thereof and a pharmaceutically acceptable carrier.

11. The pharmaceutical product of claim 1 for the treatment of nosocomial pneumonia, community-acquired pneumonia, urinary tract infection, complicated intra-abdominal infection, complicated skin/skin structure infection, infectious exacerbations of cystic fibrosis, sepsis, melioidosis.

12. The pharmaceutical product of claim 1 wherein said combination contains one carbapenem antibiotic, or its pharmaceutically acceptable salt.

13. The pharmaceutical product of claim 8 wherein the weight ratio of monobactam antibiotic or its salt to the carbapenem antibiotic and its salt is 5:1 to 1:5.

14. The pharmaceutical product of claim 8 wherein the weight ratio of monobactam antibiotic or its salt to the carbapenem antibiotic and its salt is from 2:1 to 1:2.

15. The pharmaceutical product of claim 8 wherein said weight ratio is 1:1.

16. A packaged kit for treating bacterial infection in mammals comprising at least two dosage units of a pharmaceutical antibiotic, each dosage unit being in a separate container, one of said containers containing a monobactam antibiotic having an oxyimino moiety >C=N—O—, said antibiotic having the formula (I)

(I)

wherein the oxyimino moiety has the Z-orientation, or a pharmaceutically acceptable salt thereof and a second container containing at least one carbapenem antibiotic, selected from the group consisting of Meropenem, Imipenem, Ertapenem, Doripenem, or a pharmaceutically acceptable salt thereof.

17. The packaged kit of claim 16 wherein the carbapenem antibiotic is Imipenem or a pharmaceutically acceptable salt thereof.

18. The packaged kit of claim 16 wherein the carbapenem antibiotic is Meropenem or a pharmaceutically acceptable salt thereof.

19. The packaged kit of claim 16 wherein the carbapenem antibiotic is Ertapenem or a pharmaceutically acceptable salt thereof.

20. The packaged kit of claim 16 wherein the carbapenem antibiotic is Doripenem or a pharmaceutically acceptable salt thereof.

* * * * *